US012622650B2

(12) United States Patent
Attia

(10) Patent No.: US 12,622,650 B2
(45) Date of Patent: May 12, 2026

(54) SYSTEM AND A METHOD FOR ELECTROCARDIOGRAPHIC PREDICTION OF COMPUTED TOMOGRAPHY-BASED HIGH CORONARY CALCIUM SCORE (CAC)

(71) Applicant: Mayo Foundation for Medical Education and Research, Rochester, MN (US)

(72) Inventor: Itzhak Zachi Attia, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 114 days.

(21) Appl. No.: 18/642,012

(22) Filed: Apr. 22, 2024

(65) Prior Publication Data

US 2024/0277301 A1 Aug. 22, 2024

Related U.S. Application Data

(63) Continuation of application No. PCT/US2023/022325, filed on May 16, 2023.
(Continued)

(51) Int. Cl.
*A61B 5/00* (2006.01)
*A61B 5/346* (2021.01)
(Continued)

(52) U.S. Cl.
CPC ............ *A61B 5/7278* (2013.01); *A61B 5/346* (2021.01); *A61B 5/7267* (2013.01); *G16H 10/60* (2018.01); *G16H 50/20* (2018.01)

(58) Field of Classification Search
CPC ..... A61B 5/7278; A61B 5/346; A61B 5/7267; G16H 10/60; G16H 50/20
See application file for complete search history.

(56) References Cited

U.S. PATENT DOCUMENTS

| | | | |
|---|---|---|---|
| 5,655,540 A | 8/1997 | Seegobin | |
| 2007/0099239 A1* | 5/2007 | Tabibiazar | ............ G16B 40/20 |
| | | | 435/7.1 |

(Continued)

FOREIGN PATENT DOCUMENTS

| | | |
|---|---|---|
| KR | 20220040516 A | 3/2022 |
| WO | 2021162490 A2 | 8/2021 |

(Continued)

OTHER PUBLICATIONS

Han et al. Artificial Intelligence-Enabled ECG Algorithm for the Prediction of Coronary Artery Calcification, published Apr. 6, 2022; Front Cardiovasc Med. 2022; 9: 849223. (Year: 2022).*
(Continued)

*Primary Examiner* — Sana Sahand
(74) *Attorney, Agent, or Firm* — CALDWELL LLC

(57) ABSTRACT

Provided herein are methods, systems, and computer program products for the detection and evaluation of coronary artery calcium (CAC) (e.g., CAC scoring) comprising receiving voltage-time data of a plurality of leads of an electrocardiograph subject; generating a feature vector from the voltage-time data; providing the feature vector to a pretrained learning system; and receiving from the pretrained learning system an indication of the level of coronary artery calcium in the subject.

20 Claims, 7 Drawing Sheets

Related U.S. Application Data

(60) Provisional application No. 63/342,275, filed on May 16, 2022.

(51) Int. Cl.
 _G16H 10/60_ (2018.01)
 _G16H 50/20_ (2018.01)

(56) References Cited

U.S. PATENT DOCUMENTS

| | | | |
|---|---|---|---|
| 2022/0000410 A1* | 1/2022 | Baram | G06V 10/25 |
| 2022/0022836 A1 | 1/2022 | Contijoch et al. | |

FOREIGN PATENT DOCUMENTS

| | | |
|---|---|---|
| WO | 2022081646 A1 | 4/2022 |
| WO | 2023212297 A1 | 11/2023 |
| WO | 2023224948 A1 | 11/2023 |

OTHER PUBLICATIONS

Awasthi et al; Identification and risk stratification of coronary disease by artificial intelligence-enabled ECG; eClinicalMedicine, vol. 65, Nov. 2023, 102259.

Eem et al; Deep-Learning Model to Predict Coronary Artery Calcium Scores in Humans from Electrocardiogram Data; Appl. Sci. 2020, 10(23), 8746, Published: Dec. 7, 2020.

International Search Report; PCT/US2023/022325; Aug. 15, 2023; By Authorized Officer: Kari Rodriquez.

\* cited by examiner

| | Sensitivity | Specificity | Accuracy | OR (95% CI) |
|---|---|---|---|---|
| Age <65 | | | | |
| ECG-AI | 83.64 (80.08-86.79) | 40.54 (39.36-41.73) | 43.52 (42.37-44.68) | 3.49 (2.73-4.44) |
| EXG-AI Age + Sex | 80.00 (76.20-83.44) | 47.59 (46.38-48.80) | 49.83 (48.76-51.00) | 3.63 (2.90-4.55) |
| ECG-AI + CV Risk Factors | 37.17 (32.90-41.60) | 83.14 (82.22-84.03) | 79.96 (79.01-80.88) | 2.91 (2.41-3.54) |
| Age ≥65 | | | | |
| ECG-AI | 95.27 (93.10-96.92) | 18.69 (16.78-21.30) | 45.84 (43.29-48.41) | 4.63 (3.01-7.15) |
| EXG-AI Age + Sex | 93.57 (91.13-95.51) | 22.33 (19.73-25.09) | 47.49 (45.03-50.16) | 4.18 (2.86-6.11) |
| ECG-AI + CV Risk Factors | 74.48 (70.54-78.14) | 53.17 (49.96-56.36) | 60.72 (58.19-63.21) | 3.31 (2.62-4.18) |
| Men | | | | |
| ECG-AI | 91.55 (89.46-93.34) | 27.66 (26.42-28.93) | 36.94 (35.69-38.20) | 4.14 (3.22-5.32) |
| EXG-AI Age + Sex | 89.05 (86.74-91.08) | 34.44 (33.11-35.78) | 42.37 (41.09-43.65) | 4.27 (3.41-5.35) |
| ECG-AI + CV Risk Factors | 56.55 (48.49-63.27) | 75.49 (74.27-76.68) | 72.74 (71.57-73.88) | 4.01 (3.45-4.66) |
| Women | | | | |
| ECG-AI | 80.98 (74.55-86.38) | 56.59 (54.59-58.28) | 58.07 (56.23-59.89) | 5.52 (3.79-8.05) |
| EXG-AI Age + Sex | 77.72 (71.01-83.51) | 62.81 (60.95-64.65) | 63.77 (61.98-65.54) | 5.90 (4.13-8.41) |
| ECG-AI + CV Risk Factors | 55.98 (48.49-63.27) | 86.49 (85.14-87.77) | 84.53 (83.15-85.84) | 8.14 (5.96-11.12) |
| No CV Risk Factors | | | | |
| ECG-AI | 82.64 (77.96-86.68) | 41.43 (40.0-42.87) | 44.03 (42.64-45.43) | 3.37 (2.50-4.54) |
| EXG-AI Age + Sex | 77.81 (72.78-82.31) | 48.83 (47.38-50.28) | 50.66 (49.25-52.07) | 3.35 (2.55-4.40) |
| ECG-AI + CV Risk Factors | 35.05 (29.75-40.63) | 84.55 (83.47-85.58) | 81.42 (80.30-82.50) | 2.95 (2.31-3.78) |
| 1-3 CV Risk Factors | | | | |
| ECG-AI | 90.93 (87.72-93.53) | 35.52 (33.52-37.56) | 44.20 (42.28-46.13) | 5.52 (3.90-7.83) |
| EXG-AI Age + Sex | 89.71 (86.34-92.48) | 41.03 (38.96-43.12) | 48.66 (46.72-50.60) | 6.06 (4.36-8.44) |
| ECG-AI + CV Risk Factors | 59.80 (54.87-64.60) | 75.68 (73.83-77.46) | 73.20 (71.45-74.89) | 4.63 (3.71-5.77) |
| 4-5 CV Risk Factors | | | | |
| ECG-AI | 95.08 (92.02-97.22) | 23.22 (20.36-26.27) | 42.81 (39.88-45.77) | 5.85 (3.39-10.07) |
| EXG-AI Age + Sex | 92.79 (89.28-95.42) | 28.38 (25.30-31.61) | 45.93 (42.98-48.91) | 5.10 (3.22-8.07) |
| ECG-AI + CV Risk Factors | 73.77 (68.45-78.62) | 59.83 (56.37-63.22) | 63.63 (60.73-66.45) | 4.19 (3.13-5.60) |

FIG. 4 (Cont.)

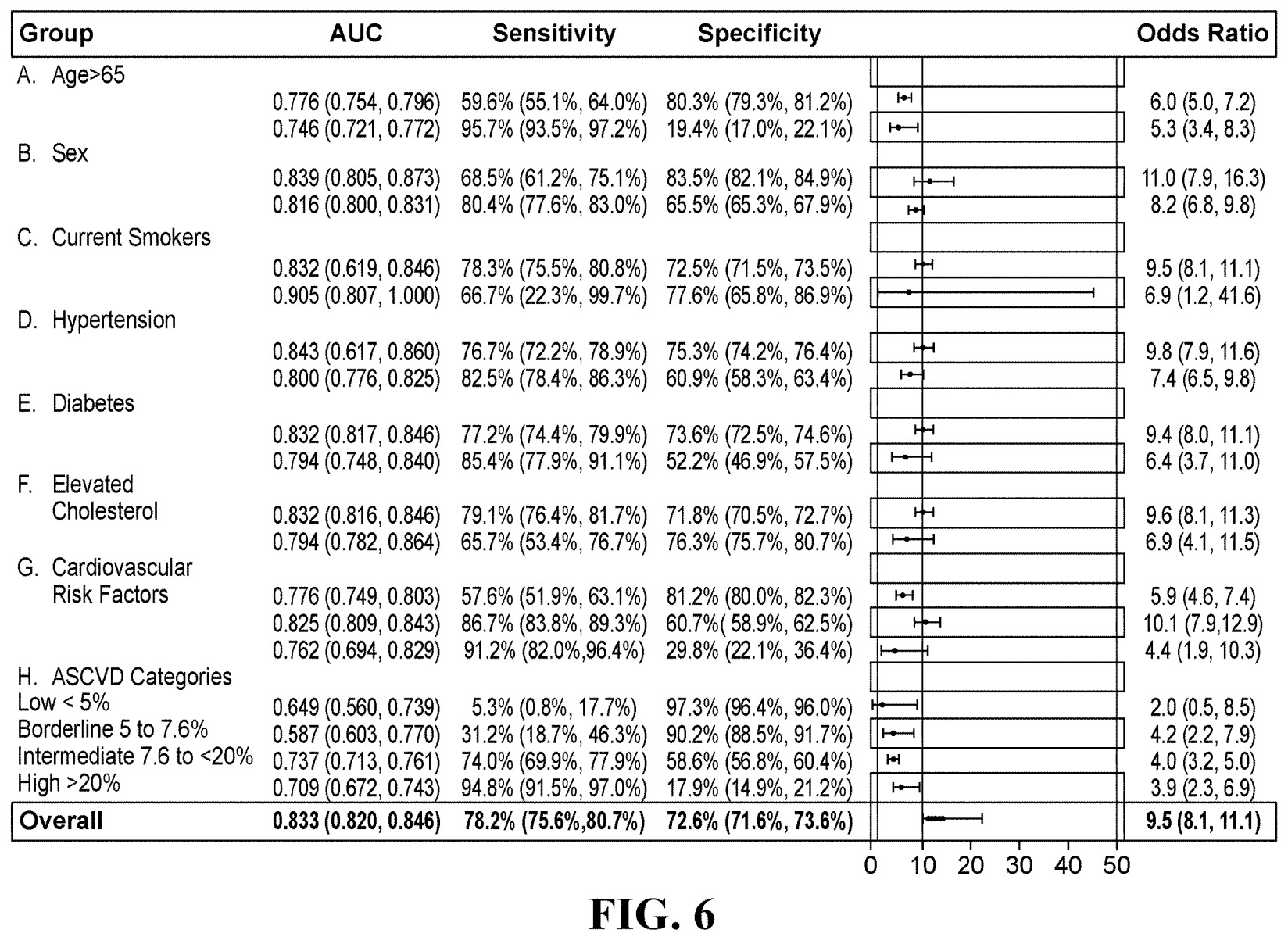

| Group | AUC | Sensitivity | Specificity | | Odds Ratio |
|---|---|---|---|---|---|
| A. Age>65 | 0.776 (0.754, 0.796) | 59.6% (55.1%, 64.0%) | 80.3% (79.3%, 81.2%) | | 6.0 (5.0, 7.2) |
| | 0.746 (0.721, 0.772) | 95.7% (93.5%, 97.2%) | 19.4% (17.0%, 22.1%) | | 5.3 (3.4, 8.3) |
| B. Sex | 0.839 (0.805, 0.873) | 68.5% (61.2%, 75.1%) | 83.5% (82.1%, 84.9%) | | 11.0 (7.9, 16.3) |
| | 0.816 (0.800, 0.831) | 80.4% (77.6%, 83.0%) | 65.5% (65.3%, 67.9%) | | 8.2 (6.8, 9.8) |
| C. Current Smokers | 0.832 (0.619, 0.846) | 78.3% (75.5%, 80.8%) | 72.5% (71.5%, 73.5%) | | 9.5 (8.1, 11.1) |
| | 0.905 (0.807, 1.000) | 66.7% (22.3%, 99.7%) | 77.6% (65.8%, 86.9%) | | 6.9 (1.2, 41.6) |
| D. Hypertension | 0.843 (0.617, 0.860) | 76.7% (72.2%, 78.9%) | 75.3% (74.2%, 76.4%) | | 9.8 (7.9, 11.6) |
| | 0.800 (0.776, 0.825) | 82.5% (78.4%, 86.3%) | 60.9% (58.3%, 63.4%) | | 7.4 (6.5, 9.8) |
| E. Diabetes | 0.832 (0.817, 0.846) | 77.2% (74.4%, 79.9%) | 73.6% (72.5%, 74.6%) | | 9.4 (8.0, 11.1) |
| | 0.794 (0.748, 0.840) | 85.4% (77.9%, 91.1%) | 52.2% (46.9%, 57.5%) | | 6.4 (3.7, 11.0) |
| F. Elevated Cholesterol | 0.832 (0.816, 0.846) | 79.1% (76.4%, 81.7%) | 71.8% (70.5%, 72.7%) | | 9.6 (8.1, 11.3) |
| | 0.794 (0.782, 0.864) | 65.7% (53.4%, 76.7%) | 76.3% (75.7%, 80.7%) | | 6.9 (4.1, 11.5) |
| G. Cardiovascular Risk Factors | 0.776 (0.749, 0.803) | 57.6% (51.9%, 63.1%) | 81.2% (80.0%, 82.3%) | | 5.9 (4.6, 7.4) |
| | 0.825 (0.809, 0.843) | 86.7% (83.8%, 89.3%) | 60.7% (58.9%, 62.5%) | | 10.1 (7.9, 12.9) |
| | 0.762 (0.694, 0.829) | 91.2% (82.0%, 96.4%) | 29.8% (22.1%, 36.4%) | | 4.4 (1.9, 10.3) |
| H. ASCVD Categories | | | | | |
| Low < 5% | 0.649 (0.560, 0.739) | 5.3% (0.8%, 17.7%) | 97.3% (96.4%, 96.0%) | | 2.0 (0.5, 8.5) |
| Borderline 5 to 7.6% | 0.587 (0.603, 0.770) | 31.2% (18.7%, 46.3%) | 90.2% (88.5%, 91.7%) | | 4.2 (2.2, 7.9) |
| Intermediate 7.6 to <20% | 0.737 (0.713, 0.761) | 74.0% (69.9%, 77.9%) | 58.6% (56.8%, 60.4%) | | 4.0 (3.2, 5.0) |
| High >20% | 0.709 (0.672, 0.743) | 94.8% (91.5%, 97.0%) | 17.9% (14.9%, 21.2%) | | 3.9 (2.3, 6.9) |
| Overall | 0.833 (0.820, 0.846) | 78.2% (75.6%, 80.7%) | 72.6% (71.6%, 73.6%) | | 9.5 (8.1, 11.1) |

Odds ratio axis: 0  10  20  30  40  50

FIG. 6

SYSTEM AND A METHOD FOR ELECTROCARDIOGRAPHIC PREDICTION OF COMPUTED TOMOGRAPHY-BASED HIGH CORONARY CALCIUM SCORE (CAC)

CROSS-REFERENCE TO RELATED APPLICATIONS

This application is a continuation of Patent Cooperation Treaty (PCT) Application No. PCT/US2023/022325, filed on May 16, 2023, and entitled "DEEP LEARNING ENABLED ELECTROCARDIOGRAPHIC PREDICTION OF COMPUTER TOMOGRAPHY-BASED HIGH CORONARY CALCIUM SCORE (CAC)", which claims the benefit of priority to U.S. Provisional Patent Application Ser. No. 63/342,275, filed on May 16, 2022, and titled "DEEP LEARNING ENABLED ELECTROCARDIOGRAPHIC PREDICTION OF COMPUTER TOMOGRAPHY-BASED HIGH CORONARY CALCIUM SCORE (CAC)", which is incorporated by reference herein in its entirety.

FIELD OF THE INVENTION

The present invention generally relates to the field of artificial intelligence. In particular, the present invention is directed to a system and a method for electrocardiographic prediction of computed tomography-based high coronary calcium score (CAC).

BACKGROUND

Embodiments of the present disclosure relate to methods for the detection and evaluation of coronary artery calcium and treatment of subjects identified for cardiovascular risk. Computed tomography-based coronary artery calcium (CAC) scoring is recommended in adults with unclear cardiovascular risk to inform preventative strategies and statin prescription. CAC has major limitations as it exposes the individual to radiation, is costly, not readily available everywhere and requires scoring by an expert radiologist. Thus, there is a long felt and unmet need for improved methods to detect and evaluate CAC.

SUMMARY OF THE DISCLOSURE

According to embodiments of the present disclosure, methods of and computer program products for the detection of coronary artery calcium and prediction of CAC score from 12-lead electrocardiograms (ECG-AI).

In some aspects of the invention, disclosed herein are methods comprising receiving voltage-time data of a subject, the voltage-time data comprising voltage data of a plurality of leads of an electrocardiograph; a feature vector from the voltage-time data; providing the feature vector to a pretrained learning system; and receiving from the pretrained learning system an indication of the level of CAC in the subject.

Aspects of the invention, as disclosed herein, also include a system comprising: an electrocardiograph comprising a plurality of leads; a computing node comprising a computer readable storage medium having program instructions embodied therewith, the program instructions executable by a processor of the computing node to cause the processor to perform a method comprising: receiving voltage-time data of a subject from the echocardiograph, the voltage-time data comprising voltage data of the plurality of leads; generating a feature vector from the voltage-time data; providing the feature vector to a pretrained learning system; and receiving from the pretrained learning system an indication of the level of CAC in the subject.

In certain aspects of the invention, disclosed herein is a computer program product for evaluation of CAC, the computer program product comprising a computer readable storage medium having program instructions embodied therewith, the program instructions executable by a processor to cause the processor to perform a method comprising: receiving voltage-time data of a subject from the echocardiograph, the voltage-time data comprising voltage data of the plurality of leads; generating a feature vector from the voltage-time data; providing the feature vector to a pretrained learning system; and receiving from the pretrained learning system an indication of the level of CAC in the subject.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 6 is a table of network ROC and sensitivity and specificity across subgroups. The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

Figure 1:
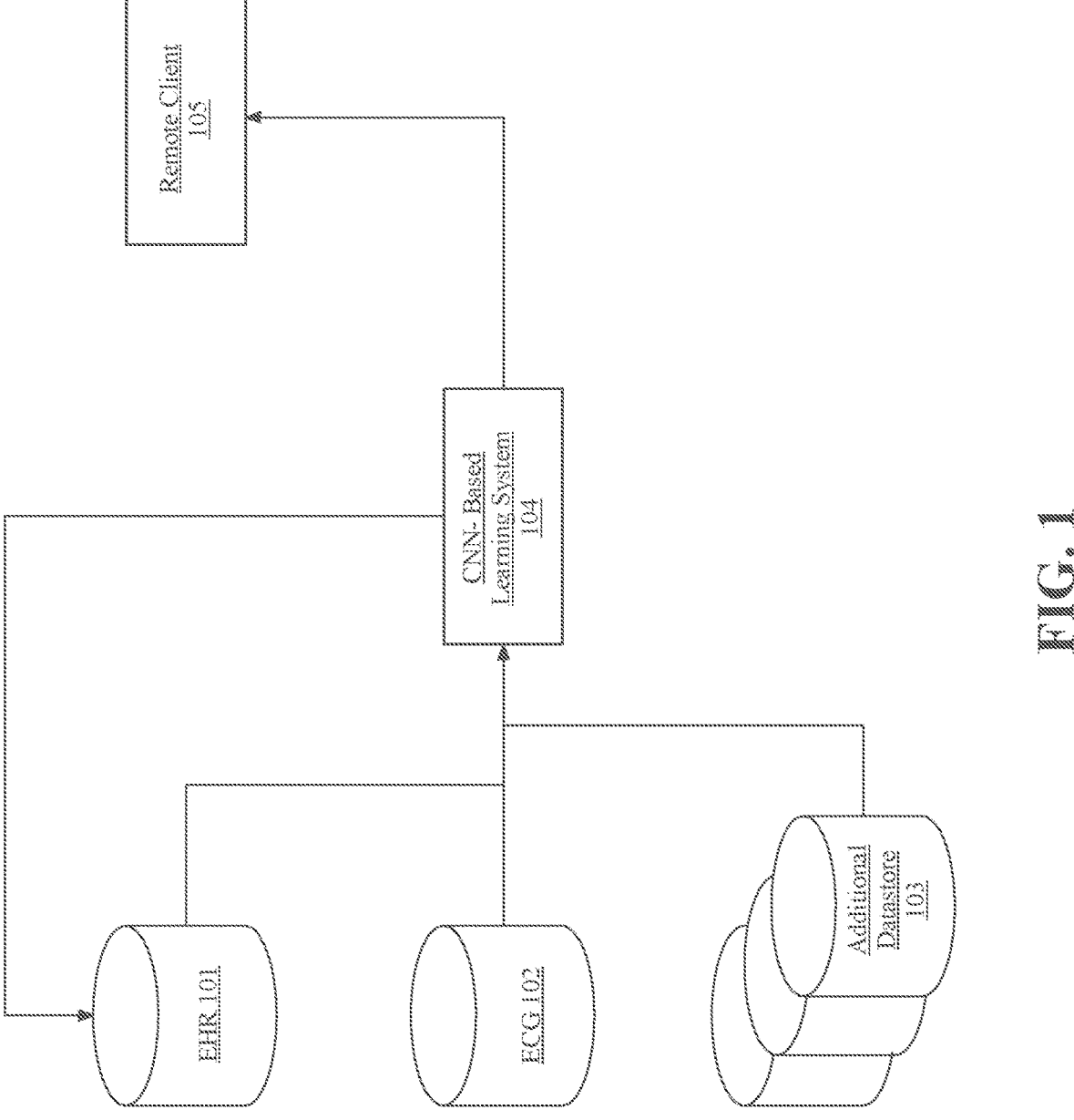
FIG. 1 is a schematic view of an exemplary embodiment of a system for detecting or otherwise predicting coronary artery calcium (CAC).

Approximately half of all deaths resulting from cardiovascular disease are caused by coronary artery disease (CAD). Patients experiencing nonfatal acute myocardial infarction or sudden death may have had no previous symptoms. Thus, identification of individuals, including asymptomatic individuals, at greater risk of experiencing future cardiovascular events is critical for the implementation of preventive strategies. Characterization of coronary-artery calcification shows equivalence with total coronary atherosclerosis load and with risk of cardiovascular events. However, acquisition and analysis of CAC data is performed by computed tomography which is expensive, requires highly specialized equipment and trained technicians, not readily accessible, and exposes the individual to radiation. Accordingly, the invention provided herein is based, at least in part, on a deep learning (DL) algorithm designed and developed to predict CAC score from 12-lead electrocardiograms (ECG-AI).

Disclosed herein is the development of an artificial intelligence (AI)-based tool to detect coronary artery calcium (CAC) from a standard 12-lead electrocardiogram (ECG). To test AI-driven models for early detection of CAC, a novel AI-electrocardiogram (ECG) network was developed.

Convolutional neural networks offer a comprehensive approach to analyzing and interpreting the vast amount of data generated in a single ECG. Algorithms were developed using 12-lead ECG data from 43,210 consecutive patients that from 1997-2020 underwent clinically indicated CAC and ECG within 1 year. In some embodiments, the invention may be performed using single-lead and 6-lead ECG subsets. Furthermore, because smartphone-enabled electrodes permit point-of-care diagnosis with single-lead and 6-lead options, compatible networks may be developed and tested.

All models used voltage-time information from 12-lead ECGs as inputs. Modeling techniques explored included convolutional neural networks with differing structures such as using all 12 leads as a single input.

Accordingly, in some aspects of the invention, disclosed herein are methods comprising receiving voltage-time data of a subject, the voltage-time data comprising voltage data of a plurality of leads of an electrocardiograph; generating a feature vector from the voltage-time data, wherein the feature vector contains a time-series of values indicating an amplitude of the voltage-time data for the plurality of leads; providing the feature vector to a pretrained learning system; and receiving from the pretrained learning system an indication of the level of CAC in the subject. Generating the feature vector may comprise generating a spectrogram based on the voltage data of the plurality of leads. In some embodiments generating the feature vector comprises grouping the voltage data of the plurality of leads into a plurality of subsets.

In some embodiments, such methods further comprise receiving demographic information of the subject, wherein generating the feature vector comprises adding the demographic information to the feature vector. In some such embodiments, the method further comprises receiving genomic information of the subject. Generating the feature vector may comprise adding the genomic information to the feature vector. Without being bound by any particular methodology or theory, said genomic data may be derived from a biological sample that is derived from a patient predisposed to increased cardiovascular risk, e.g., family history or genetic and/or protein markers. In some such embodiments, the learning system comprises a convolutional neural network. Such convolutional neural networks may comprise at least one residual connection.

In some embodiments. the voltage-time data of a subject is received from an electrocardiograph further embodiments, the voltage-time data of a subject is received from an electronic medical record.

In some embodiments, the method further comprises providing the indication to an electronic health record system for storage in a health record associated with the subject. In some embodiments, the method further comprises providing the indication to a computing node for display to a user.

In some embodiments of the methods disclosed herein, the feature vector comprises a matrix having a plurality of rows and a plurality of columns, the plurality of rows corresponding to a temporal dimension and the plurality of columns corresponding to a spatial dimension. In some such embodiments, each of the plurality of rows correspond to one of the plurality of leads and each of the plurality of columns corresponds to a timestamp. In some embodiments, the temporal dimension has a resolution of 500 Hz. The convolutional neural network disclosed herein may comprise at least nine convolutional blocks and two fully connected blocks.

In some embodiments, the period of time of the voltage-time data describes multiple cardiac cycles of the subject.

In some embodiments, the method further comprises presenting the indication of the level of CAC in the subject to a healthcare provider associated with the subject.

In some embodiments, the voltage-time data describes a single-lead ECG of the subject. In some embodiments, the single-lead ECG corresponds to one of the leads of a 12-lead ECG. In some embodiments, one of the leads of the 12-lead ECG to which the single-lead corresponds is Lead 1, Lead 2, Lead 3, AvF, AvL. AvR, or V1-V6.

In some embodiments, the voltage-time data is limited to describing a single beat of the voltage-time data from an ECG of the subject.

In some embodiments, the voltage-time data is limited to describing a single averaged beat of the voltage-time data from an ECG of the subject. In some embodiments, the voltage-time data is limited to describing a single median beat of the voltage-time data from an ECG of the subject. In some embodiments, the voltage-time data describes a single beat and the voltage-time data is multidimensional and extracted from a Vectorcardiogram. In some embodiments, the time-voltage data describes a normal sinus rhythm for the subject. In some embodiments, the feature vector is based on features of the subject's normal sinus rhythm.

In some embodiments, the time-voltage data spans a time interval that is less than or equal to thirty seconds. In some embodiments, the time-voltage data spans a time interval that is less than or equal to ten minutes.

In some embodiments, the subject is a mammal, and the mammal is a human.

In some embodiments, the time-voltage data of the subject is based on fewer than twelve leads.

In some embodiments, the indication of the level of CAC in the subject indicates at least one possible treatment plan. In some embodiments, the at least one possible monitoring or treatment plan includes administering a therapy. In some embodiments, the at least one possible treatment plan includes collecting a second series of voltage-time data.

In some embodiments, the method further comprises obtaining data describing a non-ECG profile for the mammal; generating one or more second neural network inputs representing the non-ECG profile for the subject; and processing the first neural network input along with the one or more second neural network inputs with the neural network to generate the feature vector.

In some embodiments, the indication of the level of CAC in the subject indicates at least a threshold likelihood of the subject experiencing CAC. In some embodiments, the method further comprises determining a treatment to lower the level of CAC in the subject in response to the indication of at least a threshold likelihood of the subject experiencing CAC.

In some embodiments, the voltage-time data from the subject was recorded over a first time interval, and the method further comprises obtaining a second neural network input, the second neural network input representing a second voltage-time data of the subject that was recorded over a second time interval, the first time interval and the second time interval separated by a third time interval; and processing the first neural network input along with the second neural network input with the neural network to generate the feature vector for the subject. In some embodiments, the third time interval is at least a minute, an hour, a day, a week, or a month. In some embodiments, the neural network further processes, along with the first neural network input and the second neural network input, a third neural network input that indicates a length of the third time interval between the first and second time intervals when the first voltage-time data and the second voltage-time data were recorded, respectively.

In some embodiments, the pretrained learning system is trained by receiving a training set of voltage-time data from a plurality of CAC patients. In some embodiments, the training set of voltage-time data is from one of a retrospective cohort subset or a prospective cohort subset.

In some embodiments, the voltage-time data comprises analog data characterizing ECG signals. In some embodiments, the voltage-time data comprises numerical values specifying amplitudes of ECG signals. In some embodiments, the voltage-time data comprises image data characterizing ECG signals. In some embodiments, the image data characterizing the ECG signals is in pixel form, including TIFF, PNG, or PDF file type.

With reference now to FIG. 1, a system for detecting or otherwise predicting the level of CAC is illustrated according to embodiments of the present disclosure. As outlined above, in various embodiments, patient information, including electrocardiogram (ECG) data, is provided to a learning system in order to determine the level of CAC. Thus, aspects of the invention, as disclosed herein, also include a system comprising: an electrocardiograph comprising a plurality of leads; a computing node comprising a computer readable storage medium having program instructions embodied therewith, the program instructions executable by a processor of the computing node to cause the processor to perform a method comprising: receiving voltage-time data of a subject from the echocardiograph, the voltage-time data comprising voltage data of the plurality of leads; generating a feature vector from the voltage-time data; providing the feature vector to a pretrained learning system; and receiving from the pretrained learning system an indication of the level of CAC in the subject. Generating the feature vector may comprise generating a spectrogram based on the voltage data of the plurality of leads. In some embodiments generating the feature vector comprises grouping the voltage data of the plurality of leads into a plurality of subsets.

With continued reference to FIG. 1, such systems further comprise receiving demographic information of the subject, wherein generating the feature vector comprises adding the demographic information to the feature vector. In some such embodiments, the system further comprises receiving genomic information of the subject. Generating the feature vector may comprise adding the genomic information to the feature vector. Without being bound by any particular methodology or theory, said genomic data may be derived from a biological sample that is derived from a patient predisposed to increased cardiovascular risk, e.g., family history or genetic and/or protein markers. In some such embodiments, the learning system comprises a convolutional neural network. Such convolutional neural networks may comprise at least one residual connection.

With continued reference to FIG. 1, the voltage-time data of a subject is received from an electrocardiogram further embodiments, the voltage-time data of a subject is received from an electronic medical record.

With continued reference to FIG. 1, the system further comprises providing the indication to an electronic health record system for storage in a health record associated with the subject. In some embodiments, the system further comprises providing the indication to a computing node for display to a user.

With continued reference to FIG. 1, the feature vector comprises a matrix having a plurality of rows and a plurality of columns, the plurality of rows corresponding to a temporal dimension and the plurality of columns corresponding to a spatial dimension. In some such embodiments, each of the plurality of columns correspond to one of the plurality of leads and each of the plurality of columns corresponds to a timestamp. In some embodiments, the temporal dimension has a resolution of 500 Hz. In some embodiments, the convolutional neural network comprises at least nine convolutional blocks and two fully connected blocks.

With continued reference to FIG. 1, patient data may be received from electronic health record (EHR) 101. An electronic health record (EHR), or electronic medical record (EMR), may refer to the systematized collection of patient and population electronically-stored health information in a digital format. These records can be shared across different health care settings. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information. EHR systems may be designed to store data and capture the state of a patient over time. In this way, the need to track down a patient's previous paper medical records is eliminated.

With continued reference to FIG. 1, electrocardiogram (ECG) data may be received directly from an electrocardiogram an exemplary 12-lead ECG, ten electrodes are placed on the patient's limbs and on the surface of the chest. The overall magnitude of the heart's electrical potential is then measured from twelve different angles (leads) and is recorded over a period of time (usually ten seconds). In this way, the overall magnitude and direction of the heart's electrical depolarization is captured at each moment throughout the cardiac cycle.

With continued reference to FIG. 1, additional datastores 103, may include further patient information as set out herein. Suitable datastores include databases, flat files, and other structures known in the art.

With continued reference to FIG. 1, it will be appreciated that ECG data may be stored in an EHR for later retrieval. It will also be appreciated that ECG data may be cached, rather than delivered directly to a learning system for further processing.

With continued reference to FIG. 1, learning system 104 receives patient information from one or more of EHR 101, ECG 102, and additional datastores 103. As set out above, in some embodiments, the learning system comprises a convolutional neural network. In various embodiments, the input to the convolutional neural network comprises voltage-time information an ECG, which in some embodiments is paired with additional patient information such as demographics or genetic information.

With continued reference to FIG. 1, learning system 104 may be pretrained using suitable population data as set out in the examples in order to produce an indication of the level of CAC. In some embodiments, the indication is binary. In some embodiments, the indication is a probability value, indicating the likelihood of the level of CAC given the input patient data.

With continued reference to FIG. 1, learning system 104 provides the indication of the level of CAC for storage as part of an EHR. In this way, a computer-aided diagnosis is provided, which may be referred to by a clinician. In some embodiments, learning system 104 provides the indication of the level of CAC to a remote client 105. For example, a remote client may be a health app, a cloud service, or another consumer of diagnostic data. In some embodiments, the learning system 104 is integrated into an ECG machine for immediate feedback to a user during testing.

With continued reference to FIG. 1, a feature vector is provided to a learning system. Based on the input features, the learning system generates one or more outputs. In some embodiments, the output of the learning system is a feature vector. The feature vector can contain a time-series of values indicating an amplitude of the voltage-time data for the plurality of leads.

With continued reference to FIG. 1, the learning system comprises an SVM. In other embodiments, the learning system comprises an artificial neural network. In some embodiments, the learning system is pre-trained using training data. In some embodiments training data is retrospective data. In some embodiments, the retrospective data is stored in a data store. In some embodiments, the learning system may be additionally trained through manual curation of previously generated outputs.

With continued reference to FIG. 1, the learning system, is a trained classifier. In some embodiments, the trained classifier is a random decision forest. However, it will be appreciated that a variety of other classifiers are suitable for use according to the present disclosure, including linear classifiers, support vector machines (SVM), or neural networks such as recurrent neural networks (RNN).

With continued reference to FIG. 1, suitable artificial neural networks include but are not limited to a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network.

With continued reference to FIG. 1, a convolutional neural network (CNN) is a class of feed-forward artificial neural networks applicable to analyzing visual imagery and other natural signals. A CNN consists of an input and an output layer, as well as multiple hidden layers. The hidden layers of a CNN typically consist of convolutional layers, pooling layers, fully connected layers, and normalization layers. Convolutional layers apply a convolution operation to the input, passing the result to the next layer. The convolution emulates the response of an individual neuron to stimuli. Each convolutional neuron processes data only for its receptive field.

With continued reference to FIG. 1, a convolution operation allows a reduction in free parameters as compared to a fully connected feed forward network. In particular, tiling a given kernel allows a fixed number of parameters to be learned irrespective of image size. This likewise reduces the memory footprint for a given network.

With continued reference to FIG. 1, a convolutional layer's parameters consist of a set of learnable filters (or kernels), which have a small receptive field, but extend through the full depth of the input volume. During the forward pass, each filter is convolved across the width and height of the input volume, computing the dot product between the entries of the filter and the input, and producing a 2-dimensional activation map of that filter. As a result, the network learns filters that activate when it detects some specific type of feature at some spatial position in the input.

With continued reference to FIG. 1, a kernel comprises a plurality of weights $w_1 \ldots w_9$. It will be appreciated that the sizes provided here are merely exemplary, and that any kernel dimension may be used as described herein. The kernel is applied to each tile of an input (e.g., an image). The result of each tile is an element of a feature map. It will be appreciated that if a plurality of kernels may be applied to the same input in order to generate multiple feature maps.

With continued reference to FIG. 1, stacking the feature maps for all kernels forms a full output volume of the convolution layer. Every entry in the output volume can thus also be interpreted as an output of a neuron that looks at a small region in the input and shares parameters with neurons in the same feature map.

With continued reference to FIG. 1, convolutional neural networks may be implemented in various hardware, including hardware CNN accelerators and GPUs.

Figure 2:
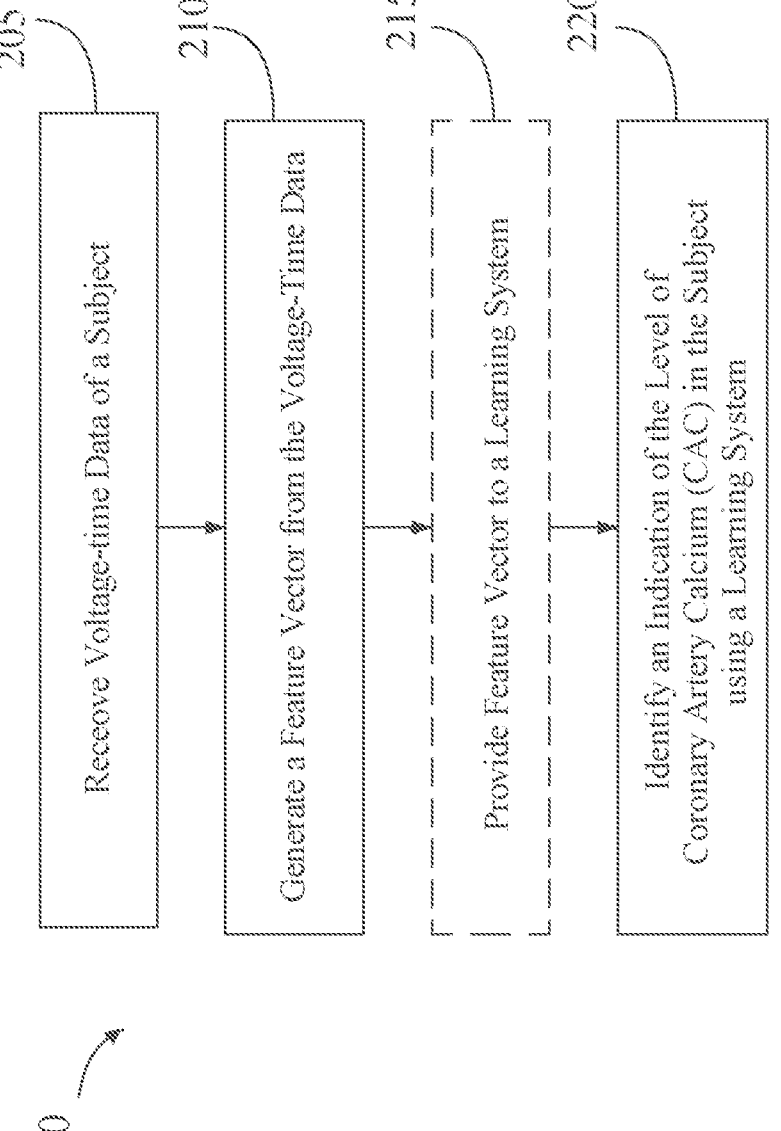
FIG. 2 is an exemplary flowchart illustrating a method of detecting or otherwise predicting CAC according to embodiments of the present disclosure.

Referring now to FIG. 2, a flowchart is provided illustrating a method of detecting or otherwise predicting the level of CAC according to embodiments of the present disclosure.

With continued reference to FIG. 2, at 205, the method includes receiving, using at least a processor, voltage-time data of a subject, wherein the voltage-time data comprises voltage data from a plurality of leads of an electrocardiograph voltage-time data may include voltage data of a plurality of leads of an electrocardiogram an embodiment, the voltage-time data of a subject may be received from an electrocardiograph and/or an electronic medical record.

With continued reference to FIG. 2, at 210, the method includes generating, using the at least a processor, a feature vector as a function of the voltage-time data, wherein the feature vector comprises one or more time-series of values indicating an amplitude of the ECG for the plurality of leads. In an embodiment, the method may include generating the feature vector comprises generating a spectrogram based on the voltage data of the plurality of leads. In another embodiment, the method may include generating the feature vector by grouping the voltage data of the plurality of leads into a plurality of subsets. In an additional embodiment, the method may include receiving, using the at least a processor, demographic data and/or genomic data associated with the subject. The method may include generating, using the at least a processor, the feature vector as a function of the demographic data and/or genomic data and the voltage-time data. In a fourth embodiment, the feature vector may include a matrix, wherein the matrix may include a plurality of rows corresponding to a temporal dimension and a plurality of columns corresponding to a spatial dimension. In some cases, each row of the plurality of rows may correspond to at least one lead of the plurality of leads. In other cases, each column of the plurality of columns may correspond to at least one timestamp.

With continued reference to FIG. 2, at 215, the method may include providing the feature vector to a pretrained learning system.

With continued reference to FIG. 2, at 220, the method includes identifying, using the at least a processor, an indication of the level of coronary artery calcium (CAC) in the subject using a learning system.

Figure 3:
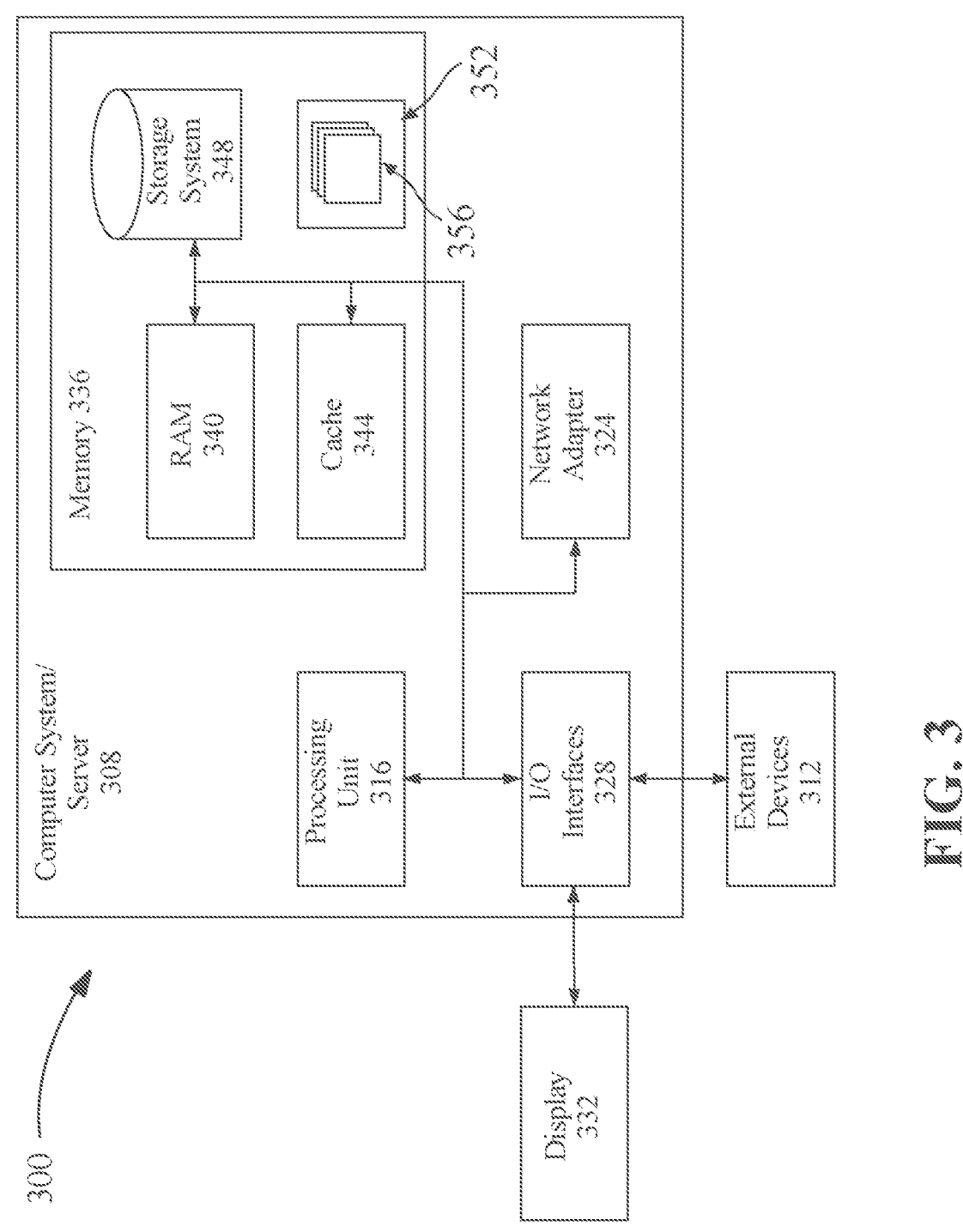
FIG. 3 is an exemplary depiction of a computing node according to an embodiment of the present disclosure.

Referring now to FIG. 3, a schematic of an example of a computing node is shown. Computing node 304 is only one example of a suitable computing node and is not intended to suggest any limitation as to the scope of use or functionality of embodiments described herein. Regardless, computing node 304 is capable of being implemented and/or performing any of the functionality set forth hereinabove.

With continued reference to FIG. 3, in computing node 304 there is a computer system/server 308, which is operational with numerous other general purpose or special purpose computing system environments or configurations. Examples of well-known computing systems, environments, and/or configurations that may be suitable for use with computer system/server 308 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

With continued reference to FIG. 3, computer system/server 308 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 308 may be practiced in distributed cloud computing environments where tasks are performed by remote processing devices that are linked through a communications network. In a distributed cloud computing environment, program modules may be located in both local and remote computer system storage media including memory storage devices.

With continued reference to FIG. 3, computer system/server 308 in computing node 304 is shown in the form of a general-purpose computing device. The components of computer system/server 308 may include, but are not limited to, one or more processors or processing units 316, a system memory 336, and a bus 320 that couples various system components including system memory 336 to processor 316.

With continued reference to FIG. 3, bus 320 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCie), and Advanced Microcontroller Bus Architecture (AMBA).

With continued reference to FIG. 3, computer system/server 308 typically includes a variety of computer system readable media. Such media may be any available media that is accessible by computer system/server 308, and it includes both volatile and non-volatile media, removable and non-removable media.

With continued reference to FIG. 3, system memory 336 can include computer system readable media in the form of volatile memory, such as random-access memory (RAM)

340 and/or cache memory 344. Computer system/server 308 may further include other removable/non-removable, volatile/non-volatile computer system storage media. By way of example only, storage system 348 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 320 by one or more data media interfaces. As will be further depicted and described below, memory 336 may include at least one program product having a set (e.g., at least one) of program modules that are configured to carry out the functions of embodiments of the disclosure.

With continued reference to FIG. 3, program/utility 352, having a set (at least one) of program modules 356, may be stored in memory 336 by way of example, and not limitation, as well as an operating system, one or more application programs, other program modules, and program data. Each of the operating system, one or more application programs, other program modules, and program data or some combination thereof, may include an implementation of a networking environment. Program modules 356 generally carry out the functions and/or methodologies of embodiments as described herein.

With continued reference to FIG. 3, computer system/server 308 may also communicate with one or more external devices 312 such as a keyboard, a pointing device, a display 332, etc.; one or more devices that enable a user to interact with computer system/server 308; and/or any devices (e.g., network card, modem, etc.) that enable computer system/server 308 to communicate with one or more other computing devices. Such communication can occur via Input/Output (I/O) interfaces 328. Still yet, computer system/server 308 can communicate with one or more networks such as a local area network (LAN), a general wide area network (WAN), and/or a public network (e.g., the Internet) via network adapter 324. As depicted, network adapter 324 communicates with the other components of computer system/server 308 via bus 320. It should be understood that although not shown, other hardware and/or software components could be used in conjunction with computer system/server 308. Examples include, but are not limited to microcode, device drivers, redundant processing units, external disk drive arrays, RAID systems, tape drives, and data archival storage systems, etc.

The present disclosure may be embodied as a system, a method, and/or a computer program product. For example, in some aspects or the invention, provided herein is a computer program product for detection and/or prediction of the level of CAC, the computer program product comprising a computer readable storage medium having program instructions embodied therewith, the program instructions executable by a processor to cause the processor to perform a method comprising: receiving voltage-time data of a subject from the echocardiograph, the voltage-time data comprising voltage data of the plurality of leads; generating a feature vector from the voltage-time data; providing the feature vector to a pretrained learning system; and receiving from the pretrained learning system an indication of the level of CAC in the subject. Generating the feature vector may comprise generating a spectrogram based on the voltage data of the plurality of leads. In some embodiments generating the feature vector comprises grouping the voltage data of the plurality of leads into a plurality of subsets.

In some embodiments, such computer program products further comprise receiving demographic information of the subject, wherein generating the feature vector comprises adding the demographic information to the feature vector. In some such embodiments, the computer program further comprises receiving genomic information of the subject. Generating the feature vector may comprise adding the genomic information to the feature vector. Without being bound by any particular methodology or theory, said genomic data may be derived from a biological sample that is derived from a patient predisposed to increased cardiovascular risk, e.g., family history or genetic and/or protein markers. In some such embodiments, the computer program product comprises a convolutional neural network. Such convolutional neural networks may comprise at least one residual connection.

In some embodiments the voltage-time data of a subject is received from an electrocardiograph further embodiments, the voltage-time data of a subject is received from an electronic medical record.

In some embodiments, the computer program product further comprises providing the indication to an electronic health record system for storage in a health record associated with the subject. In some embodiments, the computer program product further comprises providing the indication to a computing node for display to a user.

In some embodiments of the computer program product disclosed herein, the feature vector may comprise a matrix having a plurality of rows and a plurality of columns, the plurality of rows corresponding to a temporal dimension and the plurality of columns corresponding to a spatial dimension. In some such embodiments, each of the plurality of columns corresponds to one of the plurality of leads and each of the plurality of columns corresponds to a timestamp. In some embodiments, the temporal dimension has a resolution of 500 Hz. In some embodiments, the convolutional neural network comprises at least nine convolutional blocks and two fully connected blocks.

The computer program product provided herein may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program. products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Figure 5:
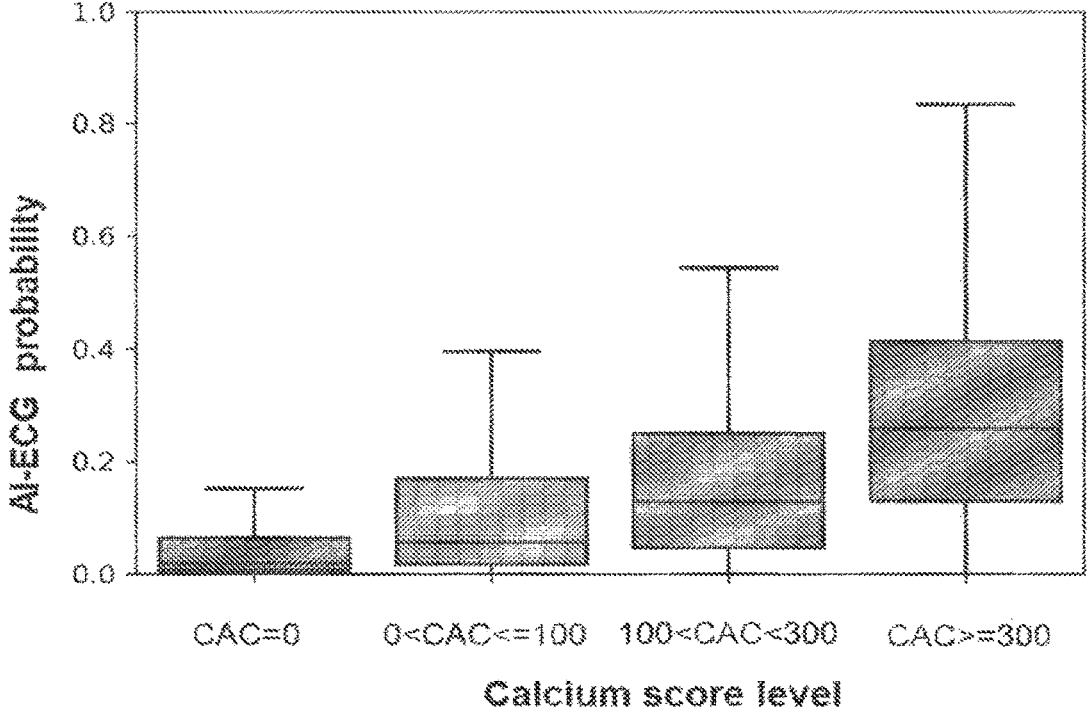
FIG. 5 is an exemplary depiction of a relationship between the AI-ECG probability and the Calcium score level.

With reference to FIG. 5, a diagram of AI-ECG probability and calcium score level is shown.

With reference to FIG. 6, a table showing network ROC, sensitivity, and specificity across subgroups is shown. Subgroups may include, as non-limiting examples, Age greater then or equal to 65, sex, smoking status, hypertension, diabetes, elevated cholesterol, cardiovascular risk factors, and ASCVD categories.

EXAMPLES

Example 1: Methods

A historical cohort of 43,210 consecutive patients that from the years 1997-2020 underwent clinically indicated CAC and ECG within 1 year was assessed. Major modifiable Cardiovascular (CV) risk factors were collected as part of preventive cardiology or general medical evaluation visits. The oldest CAC on record were used. Patients taking statins at the time of the CAC, with paced rhythm or with history of myocardial infarction or missing variables were excluded. A convolutional neural network based on ECG-AI output +/−CV risk factors to predict a high CAC score (2 300) on a random sample of 60%, and 20% of the dataset respectively was trained and validated. Model performance measures, using thresholds that yielded sensitivity of 90%, were evaluated in an independent testing set with the remaining 8,642 (20%) observations.

Definition and size of training and validation cohorts: The cohort consisted of 43,210 consecutive patients that from the years 1997-2020 underwent clinically indicated Computed tomography-based coronary artery calcium (CAC) scanning for cardiovascular risk stratification and clinically indicated electrocardiograms (ECG) within 1 year. A convolutional neural network based on ECG-AI output +/−CV risk factors to predict a high CAC score (2 300) on a random sample of 60%, and 20% of the dataset, respectively, was trained and validated. The association of the ECG-AI algorithms output was also validated to predict mortality in this cohort.

Summary of Algorithm Architecture and Design

CAC:
  Coronary artery calcium burden was quantified with CAC scoring of non-contrast ECG-gated cardiac CT images.
  Continuous 3-mm-thick images were obtained using either electron beam or multi-slice CT scanners.
  Natural language processing (NLP) algorithms were used to extract the CAC score and percentiles from the radiologist narrative reports.
  NLP output achieved a prespecified threshold of 95% accuracy.
ECG:
  For training purposes, each ECG was converted to matrix of 12×5000, where the first dimension represents the spatial leads and the second time series of ten seconds at 500 Hz.
  A Convolutional Neural Network (CNN) based model was developed using the Kerns framework with TensorFlow (Google; Mountain View, CA, USA) implemented in Python.
  This framework has been previously successfully used for created validated models that screen for Left Ventricular disfunction and age and sex estimating from standard 12-lead ECG.
  The CNN was trained to generate binary classification models based on distinct levels of CAC (i.e., >0, 2:100, 2:300) with and without tabular data (i.e., clinical characteristics).
  This CNN consisted of stacked blocks of convolutional, max pooling, and batch normalization layers interspersed with ReLU activation functions and finalized with a fully connected layer.
  Models trained for 30 epochs with 0.001 learning rate and a batch size of 32. For models that also included tabular data the same hyper-parameters and CNN architecture were used.
  Then extracted ECG features from the last CNN layer were concatenated with tabular variables prior to the activation function in the final layer.
  Models were created using (i) ECG data only, (ii) ECG data in combination with age and sex (iii) ECG data, age, sex, and cardiovascular risk factors.

Example 2: Results

Performance of the Algorithm (AUC, Sensitivity, Specificity, PPVINPV, Etc.)

The ECG-AI age and sex algorithm's area under the receiving operating characteristics curve (ROC), sensitivity, specificity, and accuracy for CAC score 2: 300 was and 0.83, 0.90%, 0.56%, 0.60%.

The ECG-AI plus age and sex algorithm displayed equivalent performance when compared to the algorithm including ECG-AI, age, sex plus major modifiable CV risk factors (Delong's p-value>0.05).

Models performance was constant across subgroups, including those with no CV risk factors.

The ECG-AI algorithms output identified individuals at an approximate average two-fold risk of death over follow-up.

This association is:

Independent of age, sex, traditional cardiovascular risk factors, current cardiovascular risk prediction algorithm, and importantly CT based CAC score +/–traditional risk factors.

The output added value i.e., identified individuals at lower or higher risk of death within most current cardiovascular risk prediction algorithm and CT based CAC score categories.

Figure 4:
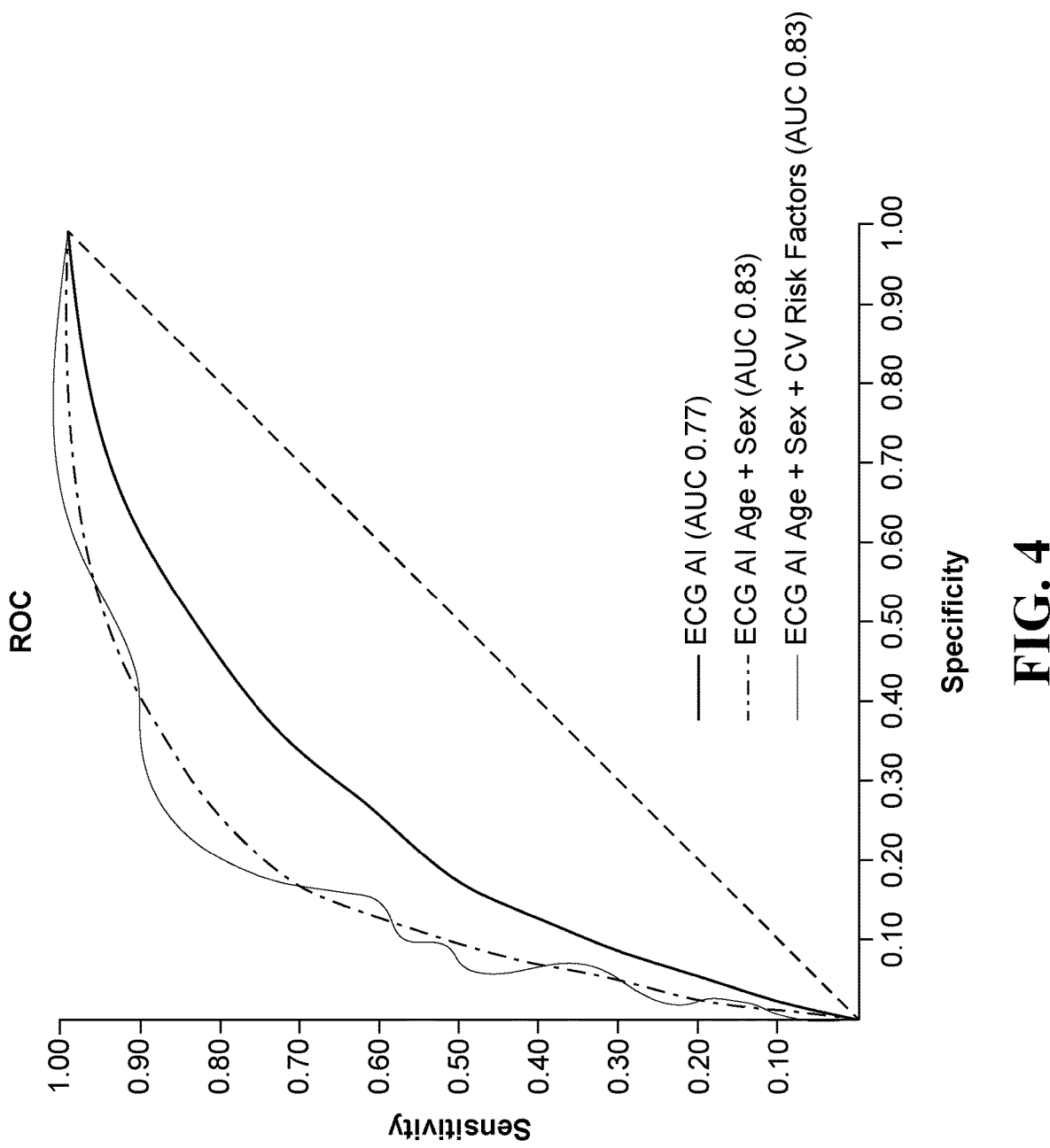
FIG. 4 is an exemplary depiction of a receiver operating characteristic curve (ROC) of the convolutional neural network used to identify patients with a CAC score 2: 300.

The ECG-AI plus age and sex algorithm displayed equivalent performance when compared to the algorithm including ECG-AI, age, sex plus major modifiable CV risk factors (see Table 1) (Delong's p-value>0.05). Models performance was constant across subgroups, including those with no CV risk factors, see FIG. 4.

Age 55±9.8

Sex, female 31%

1,857 (20%) Participants had CAC 300.

TABLE 1

| ECG-AI Performance | | | |
| --- | --- | --- | --- |
| | ROC | Sensitivity | Specificity | Accuracy |
| ECG-AI | 0.77 | 90%, | 38% | 44% |
| ECG-AI + age & sex | 0.83 | 90% | 56% | 60% |
| ECG-AI, +age & sex + other CV risk factor | 0.83 | 90% | 57% | 61% |

Algorithm's Area Under the Receiving Operating Characteristics Curve (ROC), Sensitivity, Specificity, and Accuracy for CAC Score 300

A deep learning-enabled ECG algorithm can help predict a high CAC score, even without any additional information about modifiable CV risk factors. Accordingly, the algorithm could be used to improve the selection of subjects with a higher likelihood of having a high CAC.

All publications (including patents, patent applications and sequence accession numbers mentioned herein) are hereby incorporated by reference in their entirety as if each individual publication was specifically and individually indicated to be incorporated by reference. In case of conflict, the present application, including any definitions herein, will control.

Those skilled in the art will recognize or be able to ascertain using no more than routine experimentation, many equivalents to the specific embodiments of the invention described herein. Such equivalents are intended to be encompassed by the following claims.

What is claimed is:

1. A method for electrocardiographic prediction of computed tomography-based high coronary calcium score, wherein the method comprises:

receiving, using at least a processor, voltage-time data of a subject, wherein the voltage-time data comprises image data of voltage data from a plurality of leads of an electrocardiograph characterizes electrocardiogram (ECG) signals;

generating, using the at least a processor, a feature vector as a function of the image data of the voltage-time data, wherein the feature vector comprises one or more time-series of values indicating an amplitude of an for the plurality of leads; and identifying, using the at least a processor, an indication of a level of coronary artery calcium (CAC) in the subject using a learning system comprising a convolutional neural network (CNN) by:

receiving a training set of a plurality of voltage-time data from a plurality of CAC patients, wherein the plurality of voltage-time data comprises a plurality of image data characterizing a plurality of ECG signals from the plurality of CAC patients correlated to indications comprising a probability value, indicating a likelihood of the level of CAC in a given patient;

generating, automatedly, a training matrix by converting pixels in the training set representative of each ECG of the plurality of image data of the plurality of voltage-time data to associated training matrix elements to form a training matrix of a predetermined size, wherein a first dimension of the training matrix represents spatial leads and a second dimension of the training matrix represents a time series of a predetermined time duration at a predetermined frequency;

training the CNN using the automatedly generated training matrix, wherein training the CNN comprises:

feeding the training matrix, representative of the training set, to an input layer of the CNN;

tiling the training matrix at the input layer into a plurality of tiles representative of the training matrix;

applying learnable kernels of parameters in at least one convolutional layer of the CNN across pixel data in the plurality of tiles which is representative of the plurality of image data characterizing the plurality of ECG signals in the training set, wherein a predetermined number of parameters in the at least one convolutional layer are learned irrespective of image size; and populating an output layer of the CNN based on results generated by application of the learnable kernels to the pixel data;

updating the feature vector as a function of demographic data associated with the subject and genomic data associated with the subject;

inputting, to the trained CNN, the updated feature vector representative of the subject's image data, the subject's demographic data and the subject's genomic data; and outputting, from the trained CNN, as a function of the updated feature vector, the indication of the level of CAC in the subject.

2. The method of claim 1, wherein generating the feature vector comprises generating a spectrogram as a function of the voltage data.

3. The method of claim 1, wherein generating the feature vector comprises grouping the voltage data from each lead of the plurality of leads into a plurality of subsets.

4. The method of claim 1, wherein the method further comprises:

receiving, using the at least a processor, the demographic data associated with the subject; and generating, using the at least a processor, the feature vector as a function of the demographic data and the voltage-time data.

5. The method of claim 1, wherein the method further comprises:

receiving, using the at least a processor, the genomic data associated with the subject; and generating, using the at least a processor, the feature vector as a function of the genomic data and the voltage-time data.

6. The method of claim 1, wherein the voltage-time data of the subject is received from an electronic medical record.

7. The method of claim 1, wherein the feature vector comprises a matrix, wherein the matrix comprises:

a plurality of rows corresponding to a temporal dimension; and a plurality of columns corresponding to a spatial dimension.

8. The method of claim 7, wherein each row of the plurality of rows corresponds to at least one lead of the plurality of leads.

9. The method of claim 7, wherein each column of the plurality of columns corresponds to at least one timestamp.

10. The method of claim 7, wherein the temporal dimension has a resolution of 500 Hz.

11. A system for electrocardiographic prediction of computed tomography-based high coronary calcium score (CAC), wherein the system comprises:

at least a processor;

a computer readable storage medium communicatively connected to the at least a processor, wherein the computer readable storage medium contains instructions configuring the at least a processor:

receive voltage-time data of a subject, wherein the voltage-time data comprises image data of voltage data from a plurality of leads of an electrocardiograph and characterizes electrocardiogram (ECG) signals;

generate a feature vector as a function of the image data of the voltage-time data, wherein the feature vector comprises one or more time-series of values indicating an amplitude of an ECG for the plurality of leads; and identify an indication of a level of coronary artery calcium (CAC) in the subject using a learning system comprising a convolutional neural network (CNN) by:

receiving a training set of a plurality of voltage-time data from a plurality of CAC patients, wherein the plurality of voltage-time data comprises a plurality of image data characterizing a plurality of ECG signals from the plurality of CAC patients correlated to indications comprising a probability value, indicating a likelihood of the level of CAC in a given patient;

generating, automatedly, a training matrix by converting pixels in the training set representative of each ECG of the plurality of image data of the plurality of voltage-time data to associated training matrix elements to form a training matrix of a predetermined size, wherein a first dimension of the training matrix represents spatial leads and a second dimension of the training matrix represents a time series of a predetermined time duration at a predetermined frequency;

training the CNN using the automatedly generated training matrix, wherein training the CNN comprises:

feeding the training matrix, representative of the training set, to an input layer of the CNN;

tiling the training matrix at the input layer into a plurality of tiles representative of the training matrix;

applying learnable kernels of parameters in at least one convolutional layer of the CNN across pixel data in the plurality of tiles which is representative of the plurality of image data characterizing the plurality of ECG signals in the training set, wherein a predetermined number of parameters in the at least one convolutional layer are learned irrespective of image size; and populating an output layer of the CNN based on results generated by application of the learnable kernels to the pixel data;

updating the feature vector as a function of demographic data associated with the subject and genomic data associated with the subject;

inputting, to the trained CNN, the updated feature vector representative of the subject's image data, the subject's demographic data and the subject's genomic data; and outputting, from the trained CNN, as a function of the updated feature vector, the indication of the level of CAC in the subject.

12. The system of claim 11, wherein generating the feature vector comprises generating a spectrogram as a function of the voltage data.

13. The system of claim 11, wherein generating the feature vector comprises grouping the voltage data from each lead of the plurality of leads into a plurality of subsets.

14. The system of claim 11, wherein the computer readable storage medium contains further instructions configuring the at least a processor to:

receive the demographic data associated with the subject; and generate the feature vector as a function of the demographic data and the voltage-time data.

15. The system of claim 11, wherein the computer readable storage medium contains further instructions configuring the at least a processor to:

receive the genomic data associated with the subject; and generate the feature vector as a function of the genomic data and the voltage-time data.

16. The system of claim 11, wherein the voltage-time data of the subject is received from an electronic medical record.

17. The system of claim 11, wherein the feature vector comprises a matrix, wherein the matrix comprises:

a plurality of rows corresponding to a temporal dimension; and a plurality of columns corresponding to a spatial dimension.

18. The system of claim 17, wherein each row of the plurality of rows correspond to at least one lead of the plurality of leads.

19. The system of claim 17, wherein each column of the plurality of columns corresponds to at least one timestamp.

20. The system of claim 17, wherein the temporal dimension has a resolution of 500 Hz.

\* \* \* \* \*